United States Patent

Wu et al.

[11] Patent Number: 6,017,442
[45] Date of Patent: Jan. 25, 2000

[54] HYDROCARBON CONVERSION WITH DUAL METAL PROMOTED ZEOLITE

[75] Inventors: An-hsiang Wu, Bartlesville; Charles A. Drake, Nowata, both of Okla.

[73] Assignee: Phillips Petroleum Company, Bartlesville, Okla.

[21] Appl. No.: 09/158,958

[22] Filed: Sep. 22, 1998

Related U.S. Application Data

[63] Continuation-in-part of application No. 08/933,506, Sep. 18, 1997, abandoned.

[51] Int. Cl.[7] ............................. C10G 35/06; C07C 5/41
[52] U.S. Cl. ....................... 208/137; 208/138; 585/407; 585/418; 585/419; 585/434
[58] Field of Search ..................................... 208/135, 137, 208/138; 585/407, 418, 419, 434

[56] References Cited

U.S. PATENT DOCUMENTS

| | | | |
|---|---|---|---|
| 4,177,164 | 12/1979 | Murtha et al. | 252/455 A |
| 4,670,134 | 6/1987 | Kolts et al. | 208/251 H |
| 4,691,071 | 9/1987 | Bricker | 585/319 |
| 4,698,322 | 10/1987 | Santilli et al. | 502/74 |

FOREIGN PATENT DOCUMENTS

| | | |
|---|---|---|
| WO 96/00269 | 1/1996 | WIPO . |
| WO 96/00270 | 1/1996 | WIPO . |

*Primary Examiner*—Walter D. Griffin

[57] ABSTRACT

A catalyst composition contains a zeolite, cerium or cerium oxide, and a Group VIII metal or metal oxide. The composition is produced by contacting the zeolite with compounds of the metals and then heat-treating the metals-containing zeolite. Hydrocarbons are converted to $C_6$–$C_8$ aromatic hydrocarbons by contacting the hydrocarbons with the catalyst composition at conversion conditions.

31 Claims, No Drawings

HYDROCARBON CONVERSION WITH DUAL METAL PROMOTED ZEOLITE

This application is a continuation-in-part of application Ser. No. 08/933,506, filed Sep. 18, 1997, now abandoned.

FIELD OF THE INVENTION

This invention relates to a catalyst composition useful for converting a hydrocarbon to a $C_6$ to $C_8$ aromatic hydrocarbon, to a process for producing the composition, and to a process for using the composition for converting a hydrocarbon to a $C_6$ to $C_8$ aromatic hydrocarbon.

BACKGROUND OF THE INVENTION

It is well known to those skilled in the art that aromatic hydrocarbons are a class of very important industrial chemicals which find a variety of uses in petrochemical industry. It is also well known to those skilled in the art that catalytically cracking gasoline-range hydrocarbons produces aromatic hydrocarbons such as, for example, benzene, toluene, and xylenes (hereinafter collectively referred to as BTX) in the presence of catalysts which contain a zeolite. The product of this catalytic cracking process contains a multitude of hydrocarbons including unconverted $C_5+$ alkanes, $C_5+$ alkenes, $C_5+$ cycloalkanes, or combinations of two or more thereof; lower alkanes such as methane, ethane, and propane; lower alkenes such as ethylene and propylene; and $C_9+$ aromatic compounds having 9 or more carbon atoms per molecule. Recent efforts to convert gasoline to more valuable petrochemical products have focused on improving the conversion of gasoline to more valuable aromatic hydrocarbons in the presence of zeolite catalysts. For example, a gallium-promoted zeolite ZSM-5 has been used in the so-called Cyclar Process to convert a hydrocarbon to BTX. The aromatic hydrocarbons can be useful feedstocks for producing various organic compounds and polymers. However, heavier, less useful aromatic compounds having 9 or more carbon atoms per molecule ($C_9+$ aromatic compounds) are also produced by the conversion process. Furthermore, it is well known to one skilled in the art that some hydrocarbon conversion catalysts such as the type L zeolite-based catalysts are very sensitive to sulfur poisoning by a sulfur-containing compound. See, for example, WO96/00269, WO96/00270, WO96/37298, and WO96/37299. Because the catalysts are sensitive to sulfur poisoning, the process is generally carried out under a condition such that sulfur or a sulfur compound is substantially absent. Such a condition requires substantial removal or reduction of the sulfur or sulfur compound thereby increasing operation cost of the process and, consequently, the product cost. Therefore, development of a catalyst and a process for improving the conversion of a hydrocarbon, especially in the presence of a sulfur compound, to the more valuable BTX would be a significant contribution to the art and to the economy.

SUMMARY OF THE INVENTION

An object of this invention is to provide a catalyst composition which is resistant to sulfur or a sulfur compound can be used to convert a hydrocarbon to a $C_6$ to $C_8$ aromatic hydrocarbon. Also an object of this invention is to provide a process for producing the catalyst composition. Another object of this invention is to provide a process which can employ the catalyst composition to convert a hydrocarbon to a $C_6$ to $C_8$ aromatic hydrocarbon. An advantage of the invention is that it enhances or improves the production of benzene. Another advantage of the present invention is that the catalyst and the process for converting a hydrocarbon to a $C_6$ to $C_8$ hydrocarbon can be carried out in the presence of a sulfur compound. Other objects and advantages will become more apparent as this invention is more fully disclosed hereinbelow.

According to a first embodiment of the present invention, a composition which can be used as a catalyst for converting a hydrocarbon or a hydrocarbon mixture to a $C_6$ to $C_8$ aromatic hydrocarbon is provided. The composition comprises, consists essentially of, or consists of, a zeolite having incorporated therein or impregnated thereon a promoter comprising a metal or metal oxide selected from Group VIII metals and optionally at least one metal or metal oxide selected from Group IIIB metals. The terms "Group IIIB" and "Group VIII" refer to the Periodic Table of the Elements, CRC Handbook of Chemistry and Physics, 67th edition, 1986–1987, CRC Press, Boca Raton, Fla.

According to a second embodiment of the invention, a process for producing a composition which can be used as catalyst in a hydrocarbon conversion process is provided. The process can comprise, consist essentially of, or consist of: (1) contacting a zeolite with a Group VIII metal compound and Group IIIB metal compound, under a condition sufficient to incorporate the Group VIII metal compound and Group IIIB metal compound into the zeolite to form a modified zeolite; and (2) heat-treating the modified zeolite under a condition sufficient to effect the production of a heat-treated or promoted zeolite.

According to a third embodiment of the present invention, a process which can be used for converting a saturated hydrocarbon or mixture of hydrocarbons to a $C_6$–$C_8$ aromatic hydrocarbon is provided which comprises, consists essentially of, or consists of, contacting a fluid which comprises a saturated hydrocarbon or mixture of hydrocarbons which can comprise sulfur or a sulfur-containing compound, optionally in the presence of an inert fluid, with a catalyst composition which can be the same as disclosed above in the first embodiment of the invention under a condition effective to convert a saturated hydrocarbon to a $C_6$–$C_8$ aromatic hydrocarbon.

DETAILED DESCRIPTION OF THE INVENTION

According to the first embodiment of the invention, a composition which can be used as catalyst in a hydrocarbon conversion process for converting a saturated hydrocarbon to a $C_6$–$C_8$ aromatic hydrocarbon is provided. As used herein, the term "hydrocarbon" is generally referred to, unless otherwise indicated, as one or more hydrocarbons, saturated or unsaturated, having 1 to about 30 carbon atoms, preferably 1 to about 20 carbon atoms, and most preferably 2 to 16 carbon atoms per molecule. Also preferably, the hydrocarbon is an aliphatic saturated hydrocarbon, a mixture of saturated aliphatic hydrocarbons, or a mixture of saturated aliphatic hydrocarbons and unsaturated hydrocarbons. Examples of hydrocarbons include, but are not limited to, ethane, propanes, butanes, pentanes, hexanes, heptanes, octanes, nonanes, dodecanes, gasoline, or combinations of two or more thereof. The composition can comprise, consist essentially of, or consist of, a zeolite having incorporated therein, or impregnated thereon, a selectivity-improving amount of a promoter to improve the yield of or selectivity to a $C_6$–$C_8$ aromatic hydrocarbon when the composition is used in a hydrocarbon conversion process. The term "improving" or "improve" is referred to, unless otherwise indicated, as an increased weight percent of, or percent selectivity to a $C_6$–$C_8$ aromatic hydrocarbon in the product stream of a hydrocarbon conversion process using a promoted zeolite, as compared to using a nonpromoted zeolite.

The term "metal" used herein refers to, unless otherwise indicated, both "metal" and "element" of the Periodic Table of the Elements because some elements in the Periodic Table of the Elements may not be considered as metals by those skilled in the art.

According to the first embodiment of the invention, the weight ratio of the promoter to the zeolite can be any ratio so long as the ratio can improve the yield of or selectivity to a $C_6$–$C_8$ aromatic hydrocarbon in a hydrocarbon conversion process for converting of a hydrocarbon to a $C_6$–$C_8$ aromatic hydrocarbon. Generally, the ratio can be in the range of from about 0.0001:1 to about 1:1, preferably about 0.0005:1 to about 1:1, more preferably about 0.0005:1 to about 0.5:1 and most preferably from 0.001:1 to 0.1:1 for an effective hydrocarbon conversion. Alternatively, the promoter can be present in the catalyst composition in the range of from about 0.01 to about 50, preferably about 0.05 to about 50, more preferably about 0.05 to about 30, and most preferably 0.1 to 10 grams per 100 grams of the catalyst composition.

Any promoter that, when incorporated into a zeolite, is capable of improving a hydrocarbon conversion process to a $C_6$–$C_8$ aromatic hydrocarbon can be employed in the invention. Presently, it is preferred that the promoter comprises, consists essentially of, or consists of at least one Group VIII metal and one or more Group IIIB metals. The most preferred Group VIII metal is platinum or an oxide thereof. The most preferred Group IIIB metal is a lanthanide series metal or an oxide thereof. The oxidation state of the metal can be any available oxidation state. The presently preferred Group IIIB metal is cerium. For example, in the case of a platinum or a platinum oxide, the oxidation state of platinum can be 0 (metal only), 2, 4, or combinations of two or more thereof. If a combination of metals or metal oxides is employed, the molar ratio of the second metal or metal oxide, or the third metal or metal oxide, or the fourth metal or metal oxide to the first metal or metal oxide can be in the range of about 0.01:1 to about 100:1. Presently it is preferred that the weight ratio of the Group VIII metal to the Group IIIB metal be in the range of from about 0.5:1 to about 5:1.

Any commercially available zeolite which can catalyze the conversion of a hydrocarbon to an aromatic compound can be employed in the present invention. Examples of suitable zeolites include, but are not limited to, those disclosed in Kirk-Othmer Encyclopedia of Chemical Technology, third edition, volume 15 (John Wiley & Sons, New York, 1991) and in W. M. Meier and D. H. Olson, "Atlas of Zeolite Structure Types," (Butterworth-Heineman, Boston, Mass., 3rd ed. 1992). Optionally a zeolite can be steam- and/or acid-treated before using the present invention. The presently preferred zeolites are those having large pore size such as, for example, beta zeolite, zeolite X, zeolite Y, and L zeolite. The presently preferred zeolite is a type L zeolite. Type L zeolites are synthetic zeolites. The atomic ratio of silicon to aluminum in L zeolites generally vary from about 1.0 to about 3.5.

The composition of the present invention can be prepared by combining a zeolite, a clay, a promoter, and optionally a binder in the weight ratios or percent disclosed above under any conditions sufficient to effect the production of such a composition.

According to the present invention, a zeolite, preferably L zeolite, and a binder can be well mixed at about 15 to about 100° C. under atmospheric pressure, generally in a liquid such as water or a hydrocarbon, by any means known to one skilled in the art such as stirring, blending, kneading, or extrusion, following which the resulting mixture can be dried in air at a temperature in the range of from about 20 to about 800° C., for about 0.5 to about 50 hours under any pressures that accommodate the temperatures, preferably under atmospheric pressure. Thereafter, the dried, zeolite-binder mixture can be further heat-treated at a temperature in the range of from about 200 to 1000° C., preferably about 250 to about 750° C., and most preferably 350 to 650° C. for about 1 to about 30 hours to prepare the present composition. The heat treatment can be carried out by air calcination or steaming.

Generally a zeolite, before a binder is combined with the zeolite, can also be calcined under similar conditions to remove any contaminants, if present, to prepare a calcined zeolite.

A zeolite, whether it has been calcined or contains a binder, can also be treated with steam. The treatment of a zeolite, which can contain a binder, with steam can be carried out in any suitable container or vessel known to one skilled in the art at about 100° C. to about 1000° C. for about 1 to about 30 hours under any pressure that can accommodate the temperatures to produce a steamed zeolite.

A zeolite, whether it has been steamed or not, can be treated with an acid before the preparation of the present composition. Generally, any organic acids, inorganic acids, or combinations of any two or more thereof can be used in the process of the present invention so long as the acid can reduce the aluminum content in the zeolite. The acid can also be a diluted aqueous acid solution. Examples of suitable acids include, but are not limited to, sulfuric acid, hydrochloric acid, nitric acid, phosphoric acid, formic acid, acetic acid, oxalic acid, trifluoroacetic acid, trichloroacetic acid, p-toluenesulfonic acid, methanesulfonic acid, partially or fully neutralized acids wherein one or more protons have been replaced with, for example, a metal (preferably an alkali metal) or ammonium ion, and combinations of two or more thereof. Examples of partially or fully neutralized acids include, but are not limited to, sodium bisulfate, sodium dihydrogen phosphate, potassium hydrogen tartarate, ammonium sulfate, ammonium chloride, ammonium nitrate, and combinations of two or more thereof.

Any methods known to one skilled in the art for treating a solid catalyst with an acid can be used in the acid treatment of the present invention. Generally, a zeolite material, whether or not it contains a binder, or has been steamed, can be suspended in an acid solution. The concentration of the zeolite in the acid solution can be in the range of from about 0.01 to about 700, preferably about 0.1 to about 600, more preferably about 1 to about 550, and most preferably 5 to 500 grams per liter. The amount of acid required is the amount that can maintain the solution in acidic pH during the treatment. Preferably the initial pH of the acid solution containing a zeolite is adjusted to lower than about 7, preferably lower than about 6. Upon the pH adjustment of the solution, the solution can be subjected to a treatment at a temperature in the range of from about 30° C. to about 200° C., preferably about 50° C. to about 150° C., and most preferably 70° C. to 120° C. for about 10 minutes to about 30 hours, preferably about 20 minutes to about 25 hours, and most preferably 30 minutes to 20 hours. The treatment can be carried out under a pressure in the range of from about 1 to about 10 atmospheres (atm), preferably about 1 atm so long as the desired temperature can be maintained. Thereafter, the acid-treated zeolite material can be washed with running water for 1 to about 60 minutes followed by drying, at about 50 to about 1000, preferably about 75 to about 750, and most preferably 100 to 650° C. for about 0.5 to about 15, preferably about 1 to about 12, and most preferably 1 to 10 hours, to produce an acid-leached zeolite. Any drying method known to one skilled in the art such as, for example, air drying, heat drying, spray drying, fluidized bed drying, or combinations of two or more thereof can be used.

The dried, acid-leached zeolite can also be further washed, if desired, with a mild acid solution such as, for example, ammonium nitrate which is capable of maintaining the pH of the wash solution in acidic range. The volume of the acid generally can be the same volume as that disclosed above. The mild acid treatment can also be carried out under substantially the same conditions disclosed in the acid treatment disclosed above. Thereafter, the resulting solid can be washed and dried as disclosed above.

It should be noted that, a zeolite can be acid-leached or -treated before it is treated with steam.

The dried, acid-leached zeolite, whether it has been further washed with a mild acid or not, can be either heated with steam or calcined, if desired, under a condition known to those skilled in the art. Generally such a condition can include a temperature in the range of from about 250 to about 1,000, preferably about 350 to about 750, and most preferably 450 to 650° C. and a pressure in the range of from about 0.5 to about 50, preferably about 0.5 to about 30, and most preferably 0.5 to 10 atmospheres (atm) for about 1 to about 30 hours, preferably about 2 to about 20 hours, and most preferably 3 to 15 hours.

A zeolite, a calcined zeolite, or a calcined zeolite-binder mixture, the process or treatment in the second embodiment is the same for each. For the interest of brevity, only a zeolite is described hereinbelow.

In the second embodiment of the invention, a zeolite or a zeolite-binder mixture, which could have been steamed and/or acid-leached, in a desired ionic form, regardless whether calcined or not, can be combined with a promoter by the process disclosed above for producing zeolite-binder mixture to produce the composition of the invention. The composition can also be produced by contacting a zeolite with a promoter compound, in a solution or suspension, under a condition known to those skilled in the art to incorporate a promoter compound into a zeolite. Because the methods for incorporating or impregnating a promoter compound into a zeolite a solid composition such as, for example, impregnation by incipient wetness method, are well known to those skilled in the art, the description of which is also omitted herein for the interest of brevity.

According to the second embodiment of the invention, a preferred process for producing a zeolite-containing, preferably an L zeolite-containing, composition comprises, consists essentially of, or consists of: (1) contacting a zeolite with a Group VIII and a Group IIIB compound under a condition sufficient to incorporate the Group VIII and Group IIIB compounds into the zeolite to form a modified zeolite; and (2) heat-treating the modified zeolite under a condition to effect the production of a promoted zeolite. The incorporation of a Group VIII compound and a Group IIIB compound can also be carried out sequentially.

Generally, in the first step of the process of the preferred process of the second embodiment of the invention, a zeolite can be combined with a Group VIII compound and a Group IIIB (metal) compound in any suitable weight ratios which would result in the weight ratios of a metal or metal oxide to zeolite disclosed in the first embodiment of the invention. Presently it is preferred that such combination be carried out in a suitable liquid, preferably an aqueous medium, to form an incipient wetness zeolite-metal compound mixture. The combining of a zeolite and a Group VIII compound and a Group IIIB compound can be carried out at any temperature. Generally, the temperature can be in the range of from about 15° C. to about 100° C., preferably about 20° C. to about 100° C., and most preferably 20° C. to 60° C. under any pressure, preferably atmospheric pressure, for any length so long as the metal compound and the zeolite are well mixed, generally about 1 minute to about 15 hours, preferably about 1 minute to about 5 hours.

Any Group VIII compound can be used in the present invention. The presently preferred Group VIII compound is a platinum compound. Generally, any platinum compound that can promote the combining of platinum element with a zeolite can be employed herein. Examples of suitable platinum compounds include, but are not limited to, chloroplatinic acid ($H_2PtCl_6 \cdot xH_2O$), platinum chloride (platinic chloride), platinum bromide, platinum iodine, tetramine platinum chloride ($Pt(NH_3)_4Cl_2 \cdot H_2O$ or $Pt(NH_3)_4Cl_2$), tetramine platinum nitrate ($Pt(NH_3)_4(NO_3)_2$), tetramine platinum hydroxide ($Pt(NH_3)_4(OH)_2$), tetrachlorodiamine platinum, and combinations of any two or more thereof. The oxidation state of platinum in the above-illustrated platinum compound can be any available oxidation state. The presently preferred platinum compound is chloroplatinic acid for it is readily available.

Examples of other suitable Group VIII compounds include, but are not limited to, cobalt(II) acetate, cobalt acetylacetonate, cobalt acetylacetonate, cobalt benzoylacetonate, cobalt bromide, cobalt carbonate, cobalt chloride, cobalt 2-ethylhexanoate, cobalt fluoride, cobalt fluoride, cobalt iodide, cobalt iodide, cobalt 2,3-naphthalocyanine, cobalt nitrate, cobalt oxalate, cobalt perchlorate, cobalt phthalocyanine, cobalt sulfate, cobalt thiocyanate, cobalt tungstate, nickel acetate, nickel acetylacetonate, nickel bromide, nickel carbonate, nickel chloride, nickel nitrate, nickel perchlorate, nickel phosphide, nickel sulfate, nickel sulfide, nickel titanate, palladium acetate, palladium acetylacetonate, palladium bromide, palladium iodide, palladium nitrate, palladium sulfate, palladium sulfide, rhodium acetate, rhodium acetylacetonate, rhodium bromide, rhodium chloride, rhodium nitrate, rhodium octanoate, rhodium phosphate, rhodium sulfate, rhenium nitrate, rhenium sulfate, and combinations of any two or more thereof.

Any Group IIIB compounds can be used in the first step of the preferred process of the second embodiment. Examples of suitable Group IIIB compounds include, but are not limited to, ammonium cerium nitrate, cerium acetylacetonate hydrate, cerium bromide, cerium carbonate, cerium chloride, cerium 2-ethylhexanoate, cerium fluoride, cerium iodide, cerium nitrate hexahydrate, cerium oxalate nonahydrate, cerium phosphate hydrate, cerium stearate, lanthanum acetate hydrate, lanthanum acetylacetonate hydrate, lanthanum carbonate pentahydrate, lanthanum chloride hydrate, lanthanum fluoride, lanthanum iodide, lanthanum nitrate hexahydrate, lanthanum phosphate, lanthanum sulfate, lanthanum sulfide, scandium acetate hydrate, scandium carbonate hydrate, scandium chloride, scandium fluoride, scandium hexafluoroacetylacetonate, scandium nitrate pentahydrate, scandium oxalate pentahydrate, scandium oxide, tris(butylcyclopentadienyl) yttrium, yttrium acetate hydrate, yttrium acetylacetonate trihydrate, yttrium carbonate trihydrate, yttrium chloride, yttrium 2-ethylhexanoate, yttrium fluoride, yttrium naphthoate, yttrium nitrate hexahydrate, yttrium i-propoxide, and combinations of two or more thereof. The presently preferred Group IIIB compound is cerium nitrate hexahydrate for it is readily available. As disclosed above, the metal of any metal compounds can be in any available oxidation state.

Upon completion of incorporating a Group VIII compound and a Group IIIB compound into a zeolite, a modified zeolite is formed. In the next step of the process, the modified zeolite is subject to a heat treatment. The heat treatment can be air calcining or steaming. Air calcining can be carried out under a condition sufficient to convert a metal compound to its oxide form and can include a temperature in the range of from about 300° C. to about 1000° C., preferably about 350° C. to about 750° C., and most preferably 400° C. to 650° C. under a pressure in the range of from about 1 to about 10, preferably about 1 atmospheres for a period in the range of from about 1 to about 30, preferably about 1 to about 20, and most preferably 1 to 15 hours.

Steam treatment can be carried out under a suitable condition sufficient to effect the conversion of a Group VIII compound and a Group IIIB compound, which have been incorporated into the modified zeolite, to their corresponding oxide forms. The modified zeolite can be air dried to remove most moisture content before being steam-treated. Air drying can be carried out at a temperature for about 25° C. to about 150° C. for about 1 minute to about 30 hours under any effective pressure that can maintain the necessary temperature. The air-dried modified zeolite can then be treated with steam. Generally the steam temperature can be in any suitable vessel and in the range of from about 120° C. to about 1500° C., preferably about 200° C. to about 1200° C., and most preferably 250° C. to 1000° C. The treatment period can be as short as 5 minutes to as long as about 30 hours so long as it is sufficient to convert a metal compound to its oxide form. The treatment can be carried out under a pressure which can maintain the required temperature and can be in the range of from about atmospheric pressure to about 2,000, preferably to about 1,500, and most preferably to 1000 psig.

The composition of the invention then can be, if desired, pretreated with a reducing agent before being used in a hydroconversion process. The presently preferred reducing agent is a hydrogen-containing fluid which comprises molecular hydrogen ($H_2$) in the range of from 1 to about 100, preferably about 5 to about 100, and most preferably 10 to 100 volume %. The reduction can be carried out at a temperature, in the range of from about 250° C. to about 800° C. for about 0.1 to about 10 hours preferably about 300° C. to about 700° C. for about 0.5 to about 7 hours, and most preferably 350° C. to 650° C. for 1 to 5 hours.

According to the third embodiment of the present invention, a process useful for converting a hydrocarbon to a $C_6$–$C_8$ aromatic hydrocarbon comprises, consists essentially of, or consists of contacting a fluid stream comprising a saturated hydrocarbon or a mixture of saturated hydrocarbons and, optionally, in the presence of an inert fluid with a catalyst composition under a condition sufficient to effect the conversion of a saturated hydrocarbon to an olefin. The inert fluid can be hydrogen, nitrogen, helium, argon, carbon dioxide, neon, steam, and combinations of any two or more thereof. The presently preferred inert fluid is a hydrogen-containing fluid. The inert fluid can also be fed separately into contact with a hydrocarbon and a catalyst. The catalyst composition is the same as that disclosed in the first embodiment of the invention. The term "fluid" is used herein to denote gas, liquid, vapor, or combinations of two or more thereof.

According to the invention, a hydrocarbon feed stream can also comprise dissolved sulfur or a dissolved sulfur compound in minor content. When a sulfur compound is present in the feed stream, the concentration of sulfur or the sulfur of the sulfur compound in the hydrocarbon feed can be in the range of from about 0.0001 to about 2 weight %, preferably about 0.001 to about 1 weight %, more preferably about 0.01 to about 0.5 weight %, and most preferably 0.05 to 0.1 weight % of sulfur. Any sulfur-containing compounds that are associated with a refining process can be present in the feed stream. Examples of sulfur compounds include, but are not limited to, thiophenes, thiophanes, thiophenols, sulfides, disulfides, mercaptans, mercaptides, and combinations of two or more thereof. The sulfur compounds commonly present in a hydrocarbon conversion process is a thiophenes.

Any hydrogen-containing fluid which comprises, consists essentially of, or consists of, molecular hydrogen ($H_2$) can be used in the process of this invention. This hydrogen-containing fluid can therefore contain $H_2$ in the range of from about 1 to about 100, preferably about 5 to about 100, and most preferably 10 to 100 volume %. If the $H_2$ content in the fluid is less than 100%, the remainder of the fluid may be any inert gas such as, for example, $N_2$, He, Ne, Ar, steam, or combinations of two or more thereof, or any other fluid which does not significantly affect the process or the catalyst composition used therein.

Any fluid which contains a saturated hydrocarbon as disclosed above can be used as the feed for the process of this invention. Generally, the fluid feed stream can also contain olefins, naphthenes (cycloalkanes), or some aromatic compounds.

The contacting of a fluid feed stream containing a saturated hydrocarbon with the catalyst composition can be carried out in any technically suitable manner, in a batch or semicontinuous or continuous process, under a condition effective to convert an aliphatic hydrocarbon to a $C_6$ to $C_8$ aromatic hydrocarbon. Generally, a fluid stream as disclosed above, preferably being in the vaporized state, is introduced into a suitable reactor having a fixed catalyst bed, or a moving catalyst bed, or a fluidized catalyst bed, or combinations of two or more thereof by any means known to one skilled in the art such as, for example, pressure, meter pump, and other similar means. Because a hydrocarbon conversion reactor is well known to one skilled in the art, the description of which is omitted herein for the interest of brevity. The condition can include a weight hourly space velocity (WHSV) of the fluid stream in the range of about 0.01 to about 100, preferably about 0.05 to about 50, and most preferably 0.1 to 30 g feed/g catalyst/hour. The gas hourly space velocity can be in the range of from about 0.01 to about 5000 $ft^3/ft^3$ catalyst/hour. Generally, the pressure can be in the range of from about 0 to about 1000 psig, preferably about 0 to about 200 psig, and most preferably 0 to 50 psig, and the temperature is about 250 to about 1000° C., preferably about 350 to about 750° C., and most preferably 450 to 650° C.

The process effluent (product) stream generally contains a light gas fraction comprising hydrogen and methane; a $C_2$–$C_3$ fraction containing ethylene, propylene, ethane, and propane; an intermediate fraction including non-aromatic compounds having greater than 3 carbon atoms; a BTX aromatic hydrocarbons fraction (benzene, toluene, ortho-xylene, meta-xylene and para-xylene); and a $C_9$+ fraction which contains aromatic compounds having 9 or more carbon atoms per molecule. Generally, the effluent can be separated into these principal fractions by any known methods such as, for example, fractionation distillation. Because the separation methods are well known to one skilled in the art, the description of which is omitted herein. The intermediate fraction can be fed to an aromatization reactor to be converted to aromatic hydrocarbons; methane, ethane, and propane can be used as fuel gas or as a feed for other reactions such as, for example, in a thermal cracking process to produce ethylene and propylene. The olefins can be recovered and further separated into individual olefins by any method known to one skilled in the art. The individual olefins can then be recovered and marketed. The BTX fraction can be further separated into individual $C_6$ to $C_8$ aromatic hydrocarbon fractions. Alternatively, the BTX fraction can further undergo one or more reactions either before or after separation to individual $C_6$ to $C_8$ hydrocarbons so as to increase the content of the most desired BTX aromatic hydrocarbon. Suitable examples of such subsequent $C_6$ to $C_8$ aromatic hydrocarbon conversions are disproportionation of toluene (to form benzene and xylenes), transalkylation of benzene and xylenes (to form toluene), and isomerization of meta-xylene and/or ortho-xylene to para-xylene.

After the catalyst composition has been deactivated by, for example, coke deposition or feed poisons, to an extent that the feed conversion and/or the selectivity to the desired $C_6$–$C_8$ aromatic hydrocarbon(s) have become unsatisfactory, the catalyst composition can be reactivated by any means known to one skilled in the art such as, for example, calcining in air to burn off deposited coke and other carbonaceous materials, such as oligomers or polymers, preferably at a temperature of about 400 to about 650° C. The optimal time periods of the calcining depend generally on the types and amounts of deactivating deposits on the catalyst composition and on the calcination temperatures. These optimal time periods can easily be determined by those possessing ordinary skills in the art and are omitted herein for the interest of brevity.

The following examples are presented to further illustrate this invention using n-hexane as hydrocarbon feed and are not to be construed as unduly limiting the scope of the present invention. The examples illustrate the preparation of catalyst compositions of the invention and the use of the composition in a hydrocarbon conversion process.

EXAMPLE I

This example illustrates the preparation of a catalyst composition in accordance with this invention and of a catalyst compositions outside the scope of this invention.

Catalyst A (comparison) was a platinum-promoted zeolite. It was prepared as follows: 25.0 grams of a commercial L zeolite (provided by Chemie Uetikon AG, Uetikon, Switzerland, under the product designation "Zeocat® L zeolite") were mixed with 10.0 grams of Catapal® D alumina (provided by Condea Vista Company, Ceralox Division, Tucson, Ariz.), 10.0 grams of an aqueous 10 weight % acetic acid solution, 13.5 grams of water and 0.6 grams of methylcellulose. The obtained mixture was extruded so as to make extrudates of about 1/16 diameter. These extrudates were dried, first at room temperature for 16 hours and then at 125° C. for 16 hours. The dried extrudates were calcined at 538° C. for 6 hours.

A sample of 3.0 grams of the calcined alumina-bound L zeolite extrudates was impregnated with 1.80 grams of an aqueous solution containing 3.33 weight % chloroplatinic acid ($H_2PtCl_6$) and 3.33 weight % HCl. The thus-impregnated extrudates were then calcined in air at 538° C. for 6 hours. Catalyst A contained 0.76 weight % Pt.

Catalyst B (Invention) was a platinum- and cerium-promoted L zeolite. It was prepared in accordance with the procedure for Catalyst A, except that the impregnation of 3.0 grams of alumina-bound L zeolite extrudates was carried out with 1.80 grams of the aqueous solution containing 3.33 weight % $H_2PtCl_6$ and 3.33 weight % HCl and additionally with 0.10 grams of an aqueous solution containing 30 weight % $Ce(NO_3)_3.6H_2O$. The Pt/Ce-impregnated extrudates were then calcined in air at 538° C. for 5 hours. Catalyst B contained 0.74 weight % Pt and 0.32 weight % Ce.

EXAMPLE II

This example illustrates the use of the catalyst compositions described in Example I as catalysts in the conversion of hydrocarbons to olefins and BTX.

A quartz reactor tube (inner diameter: 1 centimeter; length: 60 centimeters) was filled with a bottom layer of 5 ml Alundum® alumina (inert, low surface area alumina), 2.9–3.0 grams of one of the catalysts as the middle layer, and a 5 ml top layer of Alundum® alumina. A liquid feed (density 0.67 g/cc) containing a mixture of hexane isomers (provided by Fisher Scientific Company, Fair Lawn, N.J., under the produced designation "Optima") and 50 ppm thiophene (i.e., 50 parts by weight thiophene per million parts by weight feed) was introduced into the reactor at a rate of about 20.0 ml/hour (equivalent to a weight hourly space velocity of about 4.5–4.9 wt/wt/hour). Hydrogen gas was cofed at a rate of about 300 ml/minute (thus providing a molar ratio of $H_2$ to feed hydrocarbon of about 5.2:1). The reactor had been heated to a reaction temperature of about 470° C. The reaction pressure ranged from about 55 to about 73 psig.

The reactor effluent was separated into a gaseous phase and a liquid phase by passing it through a wet ice trap for liquid product collection and then through a wet test meter for gas volume measurement. The production rate of the liquid phase was about 9 g/hour and the production rate of the gaseous phase was about 17–19 liter/hour. The liquid product was analyzed by means of a Hewlett-Packard 5890 gas chromatograph using a HP-PLOT/alumina column. Pertinent test results, attained after about 7 hours on stream, are summarized in Table I.

TABLE I

| Catalyst | % Conversion of Hexanes | Wt. % Benzene in Liquid Product | % Selectivity to Benzene |
| --- | --- | --- | --- |
| A (Comparison) | 4.29 | 3.73 | 87 |
| B (Invention) | 7.14 | 6.61 | 93 |

The test data in Table I clearly show the advantage of the Pt/Ce-promoted zeolite L catalyst over the Pt-promoted zeolite L catalyst (without Ce): higher feed conversion, higher benzene yield, and higher selectivity to benzene in the presence of 50 ppm by weight thiophene.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the disclosure and the claims.

That which is claimed is:

1. A process comprising contacting a fluid, which comprises a hydrocarbon and a sulfur compound, with a catalyst composition under a condition sufficient to effect the conversion of said hydrocarbon to a $C_6$–$C_8$ aromatic hydrocarbon wherein said catalyst composition comprises an L zeolite having incorporated therein a promoter comprising at least one Group IIIB metal or metal oxide and at least one Group VIII metal or metal oxide; and the sulfur concentration of said sulfur compound in said fluid is in the range of from about 0.0001 to about 2 weight %.

2. A process according to claim 1 wherein said Group VIII metal or metal oxide is selected from the group consisting of platinum, platinum oxides, and combinations of two or more thereof.

3. A process according to claim 1 wherein said Group IIIB metal is cerium and said Group IIIB metal oxide is cerium oxide.

4. A process according to claim 1 wherein said hydrocarbon is hexane.

5. A process according to claim 1 wherein the sulfur concentration of said sulfur compound in said fluid is in the range of from about 0.001 to about 1 weight %.

6. A process according to claim 5 wherein said catalyst composition is L zeolite having impregnated thereon platinum and cerium.

7. A process according to claim 6 wherein the weight ratio of said promoter to said L zeolite is in the range of from 0.0005:1 to 0.1:1.

8. A process according to claim 1 wherein said catalyst composition consists essentially of an L zeolite, a Group IIIB metal or metal oxide, and a Group VIII metal or metal oxide wherein the total weight of said Group VIII metal and Group IIIB metal in said composition is in the range of from about 0.01 to about 50 weight %.

9. A process according to claim 8 wherein said Group IIIB metal is cerium, Group VIII metal is platinum, and the weight % of said Group VIII metal and Group IIIB metal in said composition is in the range of from 0.1 to 10%.

10. A process according to claim 9 wherein said contacting is carried out in the presence of a hydrogen-containing fluid.

11. A process according to claim 10 wherein said condition comprises a weight hourly space velocity of said fluid in the range of about 0.01 to about 100 g feed/g catalyst/hour, a gas hourly space velocity of said hydrogen-containing fluid in the range of about 0.01 ft$^3$ gas/ft$^3$ catalyst/hour to about 5,000 ft$^3$/ft$^3$ catalyst/hour, a pressure in the range of about 0 psig to about 1000 psig, and a temperature in the range of about 250° C. to about 1000° C.

12. A process for converting an aliphatic hydrocarbon in a fluid stream to a $C_6$ to $C_8$ aromatic hydrocarbon and an olefin comprising contacting said fluid stream with a catalyst which comprises L zeolite having incorporated therein platinum and cerium wherein said fluid stream comprises about 0.001 to about 1 weight % (measured as sulfur) of a sulfur compound selected from the group consisting of thiophenes, thiophanes, thiophenols, sulfides, disulfides, mercaptans, mercaptides, and combinations of two or more thereof; and the weight hourly space velocity of said fluid stream is in the range of about 0.01 to about 100 g per g catalyst per hour and the temperature is in the range of about 400 to about 650° C.

13. A process according to claim 12 wherein said aliphatic hydrocarbon comprises hexane.

14. A process according to claim 12 wherein said sulfur compound is thiophene.

15. A process comprising contacting a fluid, which comprises at least one saturated hydrocarbon and a sulfur compound, with a catalyst composition under a condition sufficient to produce a $C_6$ to $C_8$ aromatic hydrocarbon wherein the concentration of sulfur of said sulfur compound in said fluid is in the range of from about 0.0001 to about 2 weight %; and said catalyst composition is produced by the method comprising: (1) contacting an L-zeolite with a Group VIII compound and a Group IIIB compound to produce a modified L-zeolite; and (2) heat-treating said modified L-zeolite under a condition sufficient to convert said Group VIII compound and said Group IIIB compound to their corresponding oxides to form a promoted L-zeolite.

16. A process according to claim 15 wherein said Group VIII compound is selected from the group consisting of chloroplatinic acid, platinum chloride, platinum bromide, platinum iodine, tetramine platinum chloride, tetramine platinum nitrate, tetramine platinum hydroxide, tetrachlorodiamine platinum, and combinations of two or more thereof.

17. A process according to claim 15 wherein said Group IIIB compound is selected from the group consisting of ammonium cerium nitrate, cerium acetylacetonate hydrate, cerium bromide, cerium carbonate, cerium chloride, cerium 2-ethylhexanoate, cerium fluoride, cerium iodide, cerium nitrate hexahydrate, cerium oxalate nonahydrate, cerium phosphate hydrate, cerium stearate, and combinations of two or more thereof.

18. A process according to claim 15 wherein said Group VIII compound is chloroplatinic acid.

19. A process according to claim 18 wherein said Group IIIB compound is cerium nitrate hexahydrate.

20. A process according to claim 15 wherein said sulfur compound is selected from the group consisting of thiophenes, thiophanes, thiophenols, sulfides, disulfides, mercaptans, mercaptides, and combinations of two or more thereof.

21. A process according to claim 19 wherein said sulfur compound is selected from the group consisting of thiophenes, thiophanes, thiophenols, sulfides, disulfides, mercaptans, mercaptides, and combinations of two or more thereof.

22. A process consisting essentially of contacting a fluid, which comprises an aliphatic hydrocarbon and a sulfur compound, wherein the sulfur concentration of the sulfur compound in the fluid is in the range of from about 0.0001 to about 2 weight %, with a catalyst composition under a condition to convert aliphatic hydrocarbon in the fluid stream to a $C_6$ to $C_8$ aromatic hydrocarbon and an olefin wherein the catalyst composition is produced by the method comprising: (1) contacting an L zeolite with a Group VIII compound and a Group IIIB compound to produce a modified L zeolite; and (2) heat treating said modified L zeolite under a condition sufficient to convert said Group VIII compound and Group IIIB compound to their corresponding oxides to form a promoted L zeolite wherein said Group IIIB compound is selected from the group consisting of ammonium cerium nitrate, cerium acetylacetonate hydrate, cerium bromide, cerium carbonate, cerium chloride, cerium 2-ethylhexanoate, cerium fluoride, cerium iodide, cerium nitrate hexahydrate, cerium oxalatenonahydrate, cerium phosphate hydrate, cerium stearate, and combinations of two or more thereof; and said Group VIII compound is a platinum compound.

23. A process according to claim 22 wherein said Group VIII compound is selected from the group consisting of chloroplatinic acid, platinum chloride, platinum bromide, platinum iodide, tetramine platinum chloride, tetramine platinum nitrate, tetramine platinum hydroxide, tetrachlorodiamine platinum, and combinations of two or more thereof.

24. A process according to claim 23 wherein said Group IIIB compound is cerium nitrate hexahydrate.

25. A process according to claim 24 wherein said sulfur compound is selected from the group consisting of thiophenes, thiophanes, thiophenols, sulfides, disulfides, mercaptans, mercaptides, and combinations of two or more thereof.

26. A process according to claim 25 wherein said sulfur compound is thiophene and said heat-treating in step (2) is carried out with steam.

27. A process consisting essentially of contacting a fluid, which comprises a hydrocarbon and a sulfur compound, wherein the sulfur concentration of the sulfur compound in the fluid is in the range of from about 0.0001 to about 2 weight %, with a catalyst composition under a condition sufficient to effect the conversion of said hydrocarbon to a $C_6$–$C_8$ aromatic hydrocarbon wherein said catalyst composition comprises an L zeolite having incorporated therein a promoter comprising at least one Group IIIB metal or metal oxide and at least one Group VIII metal or metal oxide.

28. A process according to claim 27 wherein said Group VIII metal or metal oxide is selected from the group consisting of platinum, platinum oxides, and combinations of two or more thereof.

29. A process according to claim 27 wherein said catalyst composition consists essentially of an L zeolite, a Group IIIB metal or metal oxide, and a Group VIII metal or metal oxide wherein the total weight of said Group VIII metal and Group IIIB metal in said composition is in the range of from 0.1 to 10%.

30. A process according to claim 29 wherein said contacting is carried out in the presence of a hydrogen-containing fluid.

31. A process according to claim 30 wherein said sulfur compound is selected from the group consisting of thiophenes, thiophanes, thiophenols, sulfides, disulfides, mercaptans, mercaptides, and combinations of two or more thereof.

* * * * *